US010993795B2

(12) United States Patent
Guo et al.

(10) Patent No.: US 10,993,795 B2
(45) Date of Patent: May 4, 2021

(54) MESH POSITIONING SYSTEM FOR LAPAROSCOPIC VENTRAL HERNIA REPAIR

(71) Applicant: Ethicon, Inc., Somerville, NJ (US)

(72) Inventors: Jianxin Guo, Livingston, NJ (US); Simon Cohn, Lebanon, NJ (US); Michael Cardinale, Morristown, NJ (US); Doug Souls, Andover, NJ (US)

(73) Assignee: Ethicon, Inc., Somerville, NJ (US)

( * ) Notice: Subject to any disclaimer, the term of this patent is extended or adjusted under 35 U.S.C. 154(b) by 56 days.

(21) Appl. No.: 16/143,740

(22) Filed: Sep. 27, 2018

(65) Prior Publication Data

US 2019/0021833 A1    Jan. 24, 2019

Related U.S. Application Data

(63) Continuation of application No. 15/222,127, filed on Jul. 28, 2016, now Pat. No. 10,117,734.

(51) Int. Cl.
| | | |
|---|---|---|
| *A61F 2/00* | (2006.01) | |
| *A61B 17/06* | (2006.01) | |
| *A61B 1/313* | (2006.01) | |
| *A61B 17/00* | (2006.01) | |

(52) U.S. Cl.
CPC ...... *A61F 2/0063* (2013.01); *A61B 17/06004* (2013.01); *A61B 1/313* (2013.01); *A61B 2017/00951* (2013.01); *A61F 2002/0072* (2013.01); *A61F 2220/005* (2013.01); *A61F 2220/0016* (2013.01); *A61F 2220/0075* (2013.01); *A61F 2230/0058* (2013.01); *A61F 2250/0059* (2013.01)

(58) Field of Classification Search
CPC .............. A61F 2/0063; A61F 2/4601; A61F 2002/0072; A61B 17/06004; A61B 17/8872
See application file for complete search history.

(56) References Cited

U.S. PATENT DOCUMENTS

| | | | | |
|---|---|---|---|---|
| 5,383,477 A | * | 1/1995 | DeMatteis | A61B 17/0057 128/898 |
| 5,397,331 A | * | 3/1995 | Himpens | A61B 17/0057 606/151 |
| 7,947,054 B2 | | 5/2011 | Eldar et al. | |
| 8,808,314 B2 | | 8/2014 | Levin | |
| 2004/0049194 A1 | | 3/2004 | Harvie et al. | |

(Continued)

FOREIGN PATENT DOCUMENTS

KR    1469643 B1    12/2014

OTHER PUBLICATIONS

International Search Report dated Oct. 2, 2017 for PCT/US2017/043040.

*Primary Examiner* — Tuan V Nguyen
(74) *Attorney, Agent, or Firm* — David R. Crichton

(57) ABSTRACT

Novel mesh implant positioning systems for use in laparoscopic body wall defect repairs, such as hernia defects, are disclosed. The systems utilize one or more bar members combined with surgical sutures and needles to position a mesh implant adjacent to a body wall defect without the need for stay sutures. Also disclosed are assemblies of the positioning systems with surgical mesh repair implants, and methods of repairing body wall defects such as hernias with the assemblies.

8 Claims, 21 Drawing Sheets

(56) References Cited

U.S. PATENT DOCUMENTS

| | | |
|---|---|---|
| 2004/0092970 A1 | 5/2004 | Xavier |
| 2009/0259260 A1 | 10/2009 | Bentley et al. |
| 2010/0292718 A1* | 11/2010 | Sholev ............. A61B 17/00234 606/151 |
| 2011/0184440 A1* | 7/2011 | Saldinger .............. A61F 2/0063 606/151 |
| 2013/0035704 A1* | 2/2013 | Dudai ................... A61F 2/0063 606/151 |
| 2014/0039527 A1 | 2/2014 | Avelar et al. |
| 2014/0155917 A1 | 6/2014 | Horton |
| 2016/0151136 A1 | 6/2016 | Hamilton et al. |

* cited by examiner

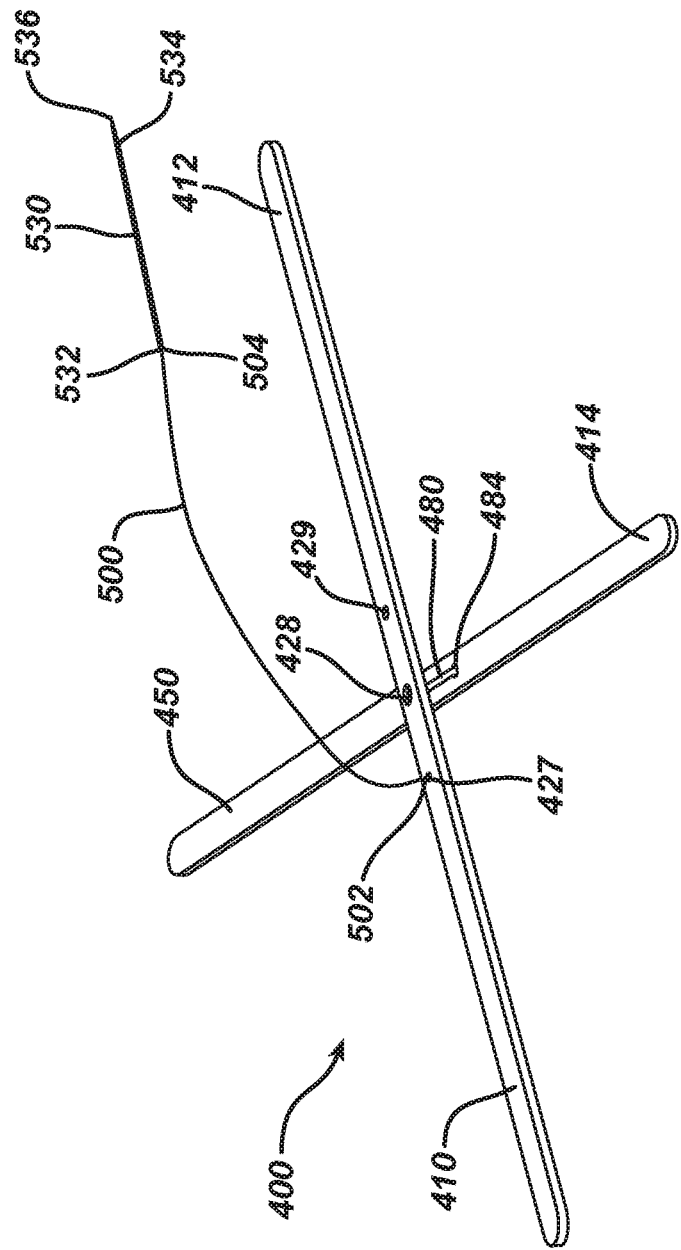

MESH POSITIONING SYSTEM FOR LAPAROSCOPIC VENTRAL HERNIA REPAIR

CROSS-REFERENCE TO RELATED APPLICATION

This application is a continuation application of U.S. application Ser. No. 15/222,127 filed on Jul. 28, 2016, now U.S. Pat. No. 10,117,734 issued on Nov. 6, 2018, the complete disclosure of which is hereby incorporated herein by reference for all purposes.

FIELD OF THE INVENTION

The field of art to which this invention pertains is medical devices and systems for repairing body wall defects, more particularly medical devices and systems for facilitating the implantation of tissue repair implants in hernia repair procedures.

BACKGROUND OF THE INVENTION

Minimally invasive laparoscopic hernia repair procedures are well known in the art. In such procedures, the surgeon is able to remotely repair a body wall tissue defect, such as a hernia, by using conventional laparoscopic surgical techniques, including the insertion of trocar cannulas through the body wall for access to the defect site, the use of a camera for remote visualization, and the use of specially designed laparoscopic surgical tools and instruments to effect the repair. Tissue repair implants have also been specially designed for such laparoscopic procedures. The use of minimally invasive laparoscopic and endoscopic surgical procedures has been found to have many documented patient benefits and advantages when compared to conventional open surgical procedures. The benefits and advantages include minimal incisions through the body wall, reduced scarring, reduced duration of the procedure and concomitant time under anesthesia, decreased opportunity for contamination of the surgical repair site with pathogens resulting in a lower incidence of hospital acquired infections, reduced pain, reduced length stay in the hospital, faster recovery time, and reduced overall costs associated with the procedure.

In a conventional endoscopic or laparoscopic ventral hernia repair procedure, the patient is anesthetized and prepared in a conventional manner. A Veress needle attached to a carbon dioxide gas source is inserted through the patient's body wall and the patient's abdominal cavity is insufflated sufficiently to provide an effective volumetric space between the body wall and the underlying viscera for both viewing and performing the surgical procedure. Next, several conventional trocar and trocar cannula combinations are penetrated through the body wall and the trocars are then withdrawn and removed from the cannulas. The cannulas serve as access ports for the insertion and removal of surgical instruments and tools, laparoscopes, various medical devices, implants, etc. A flat hernia tissue repair patch, typically mesh, is rolled or folded and inserted through the cannula and placed proximate to the hernia defect. The surgeon uses laparoscopic grasping tools to unroll or unfold the repair patch implant and place it over the hernia defect on the peritoneum. This aspect of the procedure is critical in that the implant needs to be substantially flat prior to fixation to the body wall in order to provide for an acceptable repair. The surgeon then passes several stay sutures, which were pre-mounted to the repair patch, through the abdominal wall to secure the implant over the hernia defect prior to tacking. The securement of the stay sutures requires that several open incisions be made to the exterior of the patient's body wall about the hernia or body wall defect. The surgeon then typically passes the distal end of a conventional suture passer through the partial incisions and into the patient's body cavity to retrieve the legs of each stay suture. Two passes through each incision and through the body wall are required to capture both legs of a stay suture and move them to the exterior of the body wall for securement. The legs of each suture are tensioned and are knotted together such that the knot is contained within the incision. Next, the implant is affixed to the peritoneum and body wall using a conventional laparoscopic surgical tacking instrument to complete the body wall defect repair. The procedure is completed by removing the cannulas and closing the trocar wounds, and, suturing or otherwise approximating the incisions for the stay sutures.

There is a continuing need in this art for novel and improved systems and methods for performing laparoscopic hernia repair surgical procedures such as ventral hernia repair procedures. In particular, there is a need for devices which assist the surgeon in unrolling or unfolding a tissue repair implant and maintaining the implant in a flat configuration next to the peritoneum and body wall. There is also a need to reduce the number of or eliminate stay sutures required to position a tissue repair implant prior to affixation to the peritoneum and abdominal wall in order to minimize trauma to the patient's body wall, and eliminate unnecessary incisions and associated complications such as infections and scarring.

SUMMARY OF THE INVENTION

Therefore, novel devices and methods of positioning a tissue repair implant in a laparoscopic surgical procedure are disclosed. A first aspect of the present invention is a novel positioning system for use in facilitating a laparoscopic surgical hernia repair procedure. The system has a bar member having a top side, a bottom side, a center, and a suture receiving opening centrally located in the bar member. There is a surgical suture having a distal end and a proximal end, wherein the proximal end of the suture is mounted in the suture receiving opening of the bar member such that the suture extends out from the top side of the bar member.

Another aspect of the present invention is a surgical repair assembly. The surgical repair assembly has a surgical repair mesh having a top side and a bottom side, a center, and a major axis and a minor axis. The surgical repair assembly has a positioning system. The positioning system has a bar member having a top side, a bottom side, a center, a longitudinal axis, and a suture receiving opening centrally located in the bar member. There is a surgical suture having a distal end and a proximal end, wherein the proximal end of the suture is mounted in the suture receiving opening of the bar members such that the suture extends out from the top side of the bar member. A surgical needle attached to the distal end of the suture. The top side of the bar member engages the bottom side of the mesh such that the longitudinal axis of the bar member is substantially aligned with the major axis of the mesh, and the needle and suture pass through the center of the mesh above the top side of the mesh.

Yet another aspect of the present invention is a positioning system for use in facilitating a laparoscopic surgical hernia repair procedure. The positioning system has a first bar member having a top side, a bottom side, a center, a longitudinal axis, a central suture opening aligned with the center, first and second suture openings, and a first suture slot in the bottom side. A pivot hub member extends down from the bottom side of the first bar member, said hub member having a distal end with an outwardly extending flange, a central passage in communication with the central suture opening, and opposed lateral slots in communication with the central passage and the first suture slot. The positioning system has a second bar member pivotally mounted to the first bar member. The second bar member has a top side, a bottom side, a center, a longitudinal axis, and a slot through the bar member, said slot has a first end in alignment with the center and adapted to receive the distal end of the pivot hub member, and a second end adapted to receive a suture. There is a surgical suture having a distal end and a proximal end, wherein the proximal end of the suture is mounted in the suture receiving opening such that the suture extends out from the top side of the bar member.

Still yet a further aspect of the present invention is a surgical repair assembly. The repair assembly has a surgical repair mesh having a top side and a bottom side, a center, and a major axis and a minor axis. The surgical repair assembly has a positioning system. The positioning system has a first bar member having a top side, a bottom side, a center, a longitudinal axis, a central suture opening aligned with the center, first and second suture openings, and a first suture slot in the bottom side. A pivot hub member extends down from the bottom side of the first bar member, said hub member having a distal end with an outwardly extending flange, a central passage in communication with the central suture opening, and opposed lateral slots in communication with the central passage and the first suture slot. The positioning system has a second bar member pivotally mounted to the first bar member. The second bar member has a top side, a bottom side, a center, a longitudinal axis, and a slot through the bar member, said slot having a first end in alignment with the center and adapted to receive the distal end of the pivot hub member and a second end adapted to receive a suture. There is a surgical suture having a distal end and a proximal end, wherein the proximal end of the suture is mounted in the suture receiving opening such that the suture extends out from the top side of the bar member. The top side of the first bar member engages the bottom side of the mesh such that the longitudinal axis of the top bar member is substantially aligned with the major axis of the mesh, and the longitudinal axes of the first and second bar members are substantially aligned. The suture passes through the mesh at the central suture opening and the first and second suture openings such that the suture extends out from the mesh above the central opening, and a first suture segment is formed on the top side of the mesh between the first and second suture openings, and a second suture segment is formed in the first suture slot between the second suture opening and the central suture opening.

A further aspect of the present invention includes methods of repairing a tissue wall defect in a surgical procedure using the above described positioning systems and surgical repair assemblies These and other aspects and advantages of the present invention will become more apparent from the following description and accompanying drawings.

BRIEF DESCRIPTION OF THE DRAWINGS

FIG. 19 is perspective view showing the two bars assembled into a positioning system.

DETAILED DESCRIPTION OF THE INVENTION

The novel mesh positioning systems of the present invention are manufactured from conventional biocompatible materials, including polypropylene, ABS, polyester, nylon, polyurethane, and the like. The systems may be manufactured using conventional manufacturing processes including injection molding, cutting, machining, extruding, forming, ink jet printing, punching, combinations thereof and the like. The surgical sutures useful in the practice of the present invention include conventional braided and monofilament sutures. The sutures are made from conventional absorbable and nonabsorbable biocompatible polymeric materials and combinations of such materials. The absorbable polymers may include conventional absorbable polymers including synthetic polyesters such as lactones including polylactide, polyglycolide, polydioxanone, polyglycolic acid, epsilon-caprolactone, copolymers thereof and the like. The absorbable polymers may also include conventional natural polymers such as polypeptides, collagen, etc. The nonabsorbable polymers may include conventional nonabsorbable polymers such as polypropylene, polyethylene, polyester, Nylon, etc. The surgical needles mounted to the surgical sutures will be made from conventional biocompatible materials including but not limited to surgical stainless steels. The optional adhesive sections used with the systems of the present invention may be made from conventional biocompatible adhesive polymeric materials that provide a ready release including silicones, acrylics, polyurethanes, epoxies, cyanoacrylates, and the like.

The tissue repair implants useful with the positioning systems of the present invention will typically be made from conventional surgical repair fabrics including meshes, nonwovens, films, combinations thereof, and the like. The tissue repair implants may be made from conventional biocompatible materials including absorbable polymers, nonabsorbable polymers, and combinations of absorbable and nonabsorbable polymers. The absorbable polymers may include conventional absorbable polymers including synthetic polyesters such as lactones including polylactide, polyglycolide, polydioxanone, polyglycolic acid, epsilon-caprolactone, copolymers thereof and the like. The absorbable polymers may also include conventional natural polymers such as polypeptides, collagen, etc. The nonabsorbable polymers may include conventional nonabsorbable polymers such as polypropylene, polyethylene, polyester, expanded polytetrafluoroethylene, Nylon, etc. The tissue repair implants preferably have conventional anti-adhesion barriers mounted on their visceral sides. Examples of such anti-adhesion barriers include oxidized regenerated cellulose, polyglecaprone 25, ptfe, polydioxanone, and the like.

Figure 1:
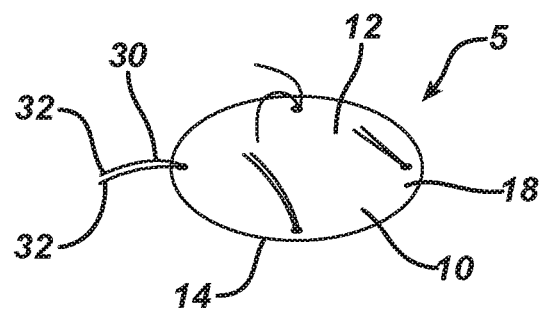
FIG. 1 is a perspective view of a hernia mesh implant of the prior art with four stay sutures mounted to the mesh for affixation to a body wall.
Figure 2:
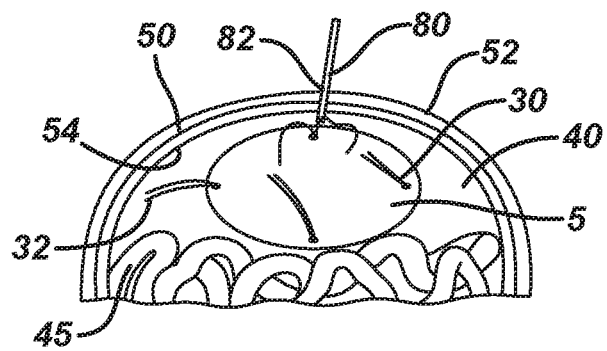
FIG. 2 is a cut-away view of an abdominal cavity showing the implant of FIG. 1 in position to be secured to the abdominal wall against the peritoneum and over a hernia defect; a suture retriever is shown penetrating the body wall in a position to catch a tail of a stay suture to move it to the exterior of the body wall for knotting and securement.
Figure 3:
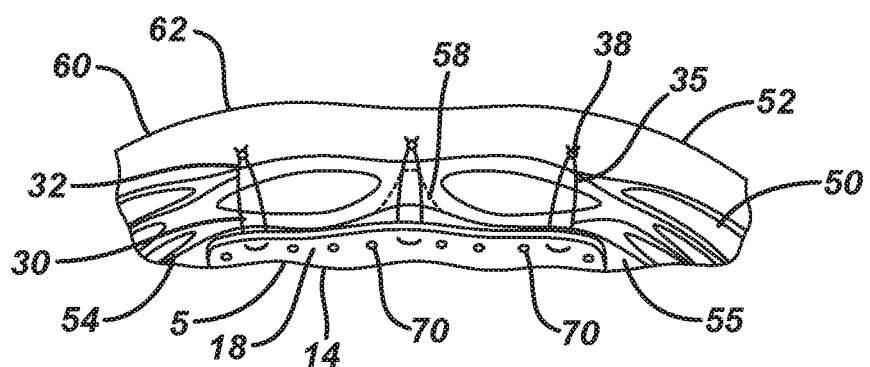
FIG. 3 is a partial magnified view of the body wall of FIG. 2 showing the implant of FIG. 1 secured to the inner side of the abdominal wall. The implant is seen to be partially secured with the stay sutures. The knots of the sutures are seen to be contained within incisions below the surface of the skin made for access by the suture passer instrument. The sutures are seen to have formed loops. The implant is also seen to have been primarily secured with conventional surgical tacks after securement with the stay sutures.

Referring initially to FIGS. 1-3, a prior art method of affixing a single layer mesh in a laparoscopic procedure wherein stay sutures are used is illustrated. Flat mesh tissue repair implant 5 is seen to have flat base member 10 having top side 12, bottom side 14 and periphery 18. The implant 5 is seen to have four stay sutures 30 mounted about the periphery 18. The sutures 30 are mounted so that two legs/limbs 32 of the sutures 30 extend upwardly through base member 10 above top side 12. As seen in FIGS. 2 and 3, the implant 5 has been moved into abdominal cavity 40 between underlying viscera 45 and the bottom side 54 of body wall 50. In order to position the repair implant 5 over a defect 58 in body wall 50, the surgeon makes cuts 62 (incisions) through the outer skin layer 60 on the top side 52 of body wall 50. The distal end 82 of a suture passer 80 is passed through the body wall 50 through skin cuts 62 and is used to retrieve the limbs 32 of the sutures such that a section of each limb 32 extends beyond the cuts 62 and outer skin layer 60. The end 82 of suture passer 80 must be passed through the body wall 50 each time a single limb 32 is retrieved. For each stay suture 30, the distal end 82 of suture retriever 80 must be passed through twice at different angles in order to retrieve both limbs 32 of suture 30 and form a suture loop 35 having knot 38 in each suture 30. Prior to forming the suture loop 35 the surgeon tensions the legs/limbs 32 to move the top side 12 of base member 10 adjacent to the peritoneum 55 on the bottom side 54 of body wall 50. The legs/limbs 32 are then tied using conventional surgical knots 38. The knots 38 are situated in the fascia underlying the outer skin layer 60. This procedure is repeated for all of the stay sutures 30 in order to properly position the implant 5 over the body wall defect 58. Once positioned, the base member 10 of the implant 5 can be affixed to the peritoneum 55 and body wall 50 using a plurality of conventional surgical tacks 70 located about the periphery 18. Although this procedure provides for satisfactory location of the implant 5 about a defect in a body wall, there are several disadvantages attendant with its use. The disadvantages include multiple skin incisions and abdominal wall punctures necessary to retrieve the ends of the stay sutures in order to form suture loops and knots to secure the mesh implant to the peritoneum or interior of the body wall. This may result in significant trauma to the tissues of the abdominal wall, and may result in pain to the patient and an extension of the post-operative healing time. The incisions and penetrations may provide pathways for hospital acquired infections. The suture loops formed in the stay sutures remain in the patient after the procedure and may produce pain during typical daily movements by the patient, even after the healing process is complete. Other disadvantages include longer operation/procedure times associated with passing the suture limbs and making conventional knots on each transfascial suture.

Figure 4:
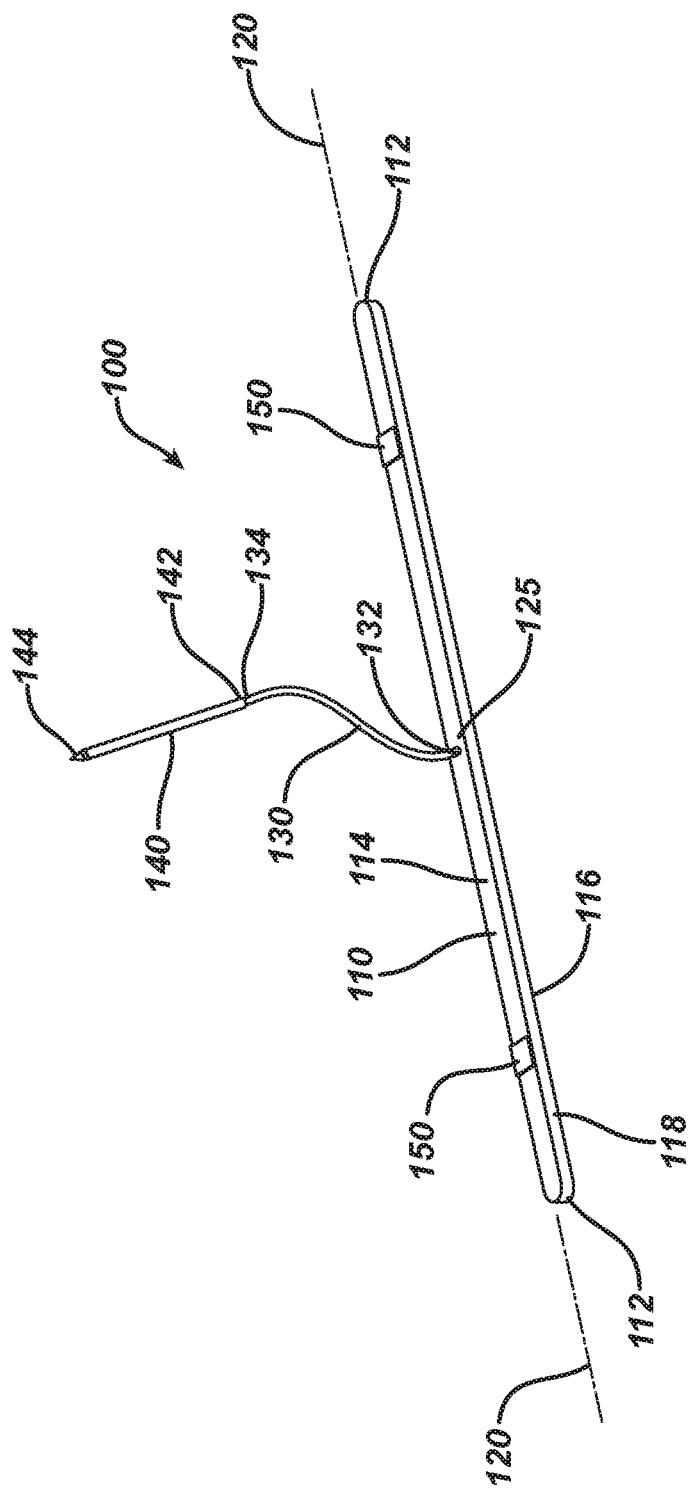
FIG. 4 is a perspective view of a positioning apparatus of the present invention having a single bar member.
Figure 5:
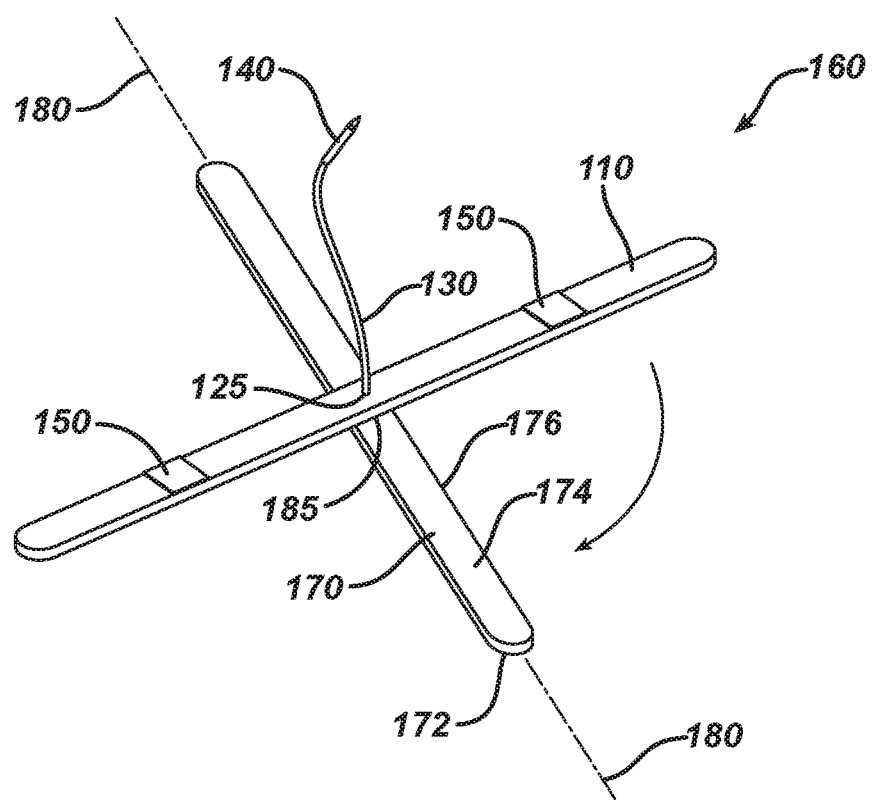
FIG. 5 is a perspective view of an alternate embodiment of a positioning apparatus of the present invention having two bar members.

Applicants' novel mesh positioning system for mesh repair implants eliminates these disadvantages since it eliminates the need for conventional stay (transfascial) sutures. As seen in FIGS. 4 and 5, two embodiments of a novel mesh positioning system of the present invention are illustrated. Referring first to FIG. 4, the mesh positioning system 100 is seen to have a bar member 110. Bar member 110 is seen to have opposed rounded ends 112. Bar member 110 has top side 114 and bottom side 116, and opposed lateral sides 118. The bar member 110 has longitudinal axis 120 and center 125. The proximal end 132 of suture 130 is seen to extend from top side 114 of bar member 110 at center 125. The proximal end 132 of suture 130 may be attached to bar member 110 in a conventional manner including gluing, knotting, welding, mechanical fasteners, etc. The distal end 134 of suture 130 is mounted to the proximal end 142 of surgical needle 140 having distal piercing point 144. Surgical needle 140 preferably has a straight configuration, but may have other configurations including curved. Adhesive sections 150 are seen on top side 114 on either end of bar member 110. The adhesive sections 150 may consist of coatings, tapes, patches, etc. An alternative embodiment of a mesh positioning system 160 of the present invention is seen in FIG. 5. Positioning system 160 is seen to have top bar member 110 pivotally mounted in a conventional manner to bottom bar member 170 such that bar member 110 and bar member 170 may be rotated with respect to each other. Bar member 170 is seen to have opposed rounded ends 172. Bar member 170 has top side 174 and bottom side 176, and opposed lateral sides 178. The bar member 110 has longitudinal axis 180 and center 185. The bar members 110 and 170 are pivotally connected at their centers 125 and 185, respectively. Surgical suture 130 with attached surgical needle 140 is seen to be affixed to and extend from bar member 130 in a similar manner as that described above.

Figure 6:
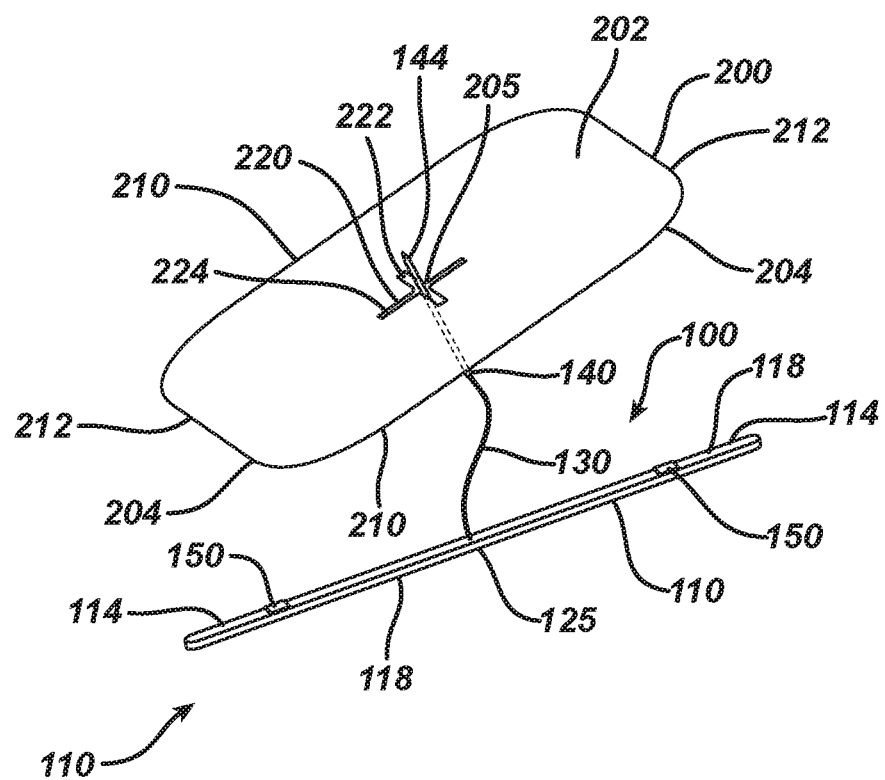
FIG. 6 is a perspective view illustrating the initial step in mounting the novel positioning system of FIG. 4 to a conventional flat single layer mesh implant suitable for a laparoscopic ventral hernia repair; the needle tip has penetrated the center of the mesh from the bottom side.
Figure 7:
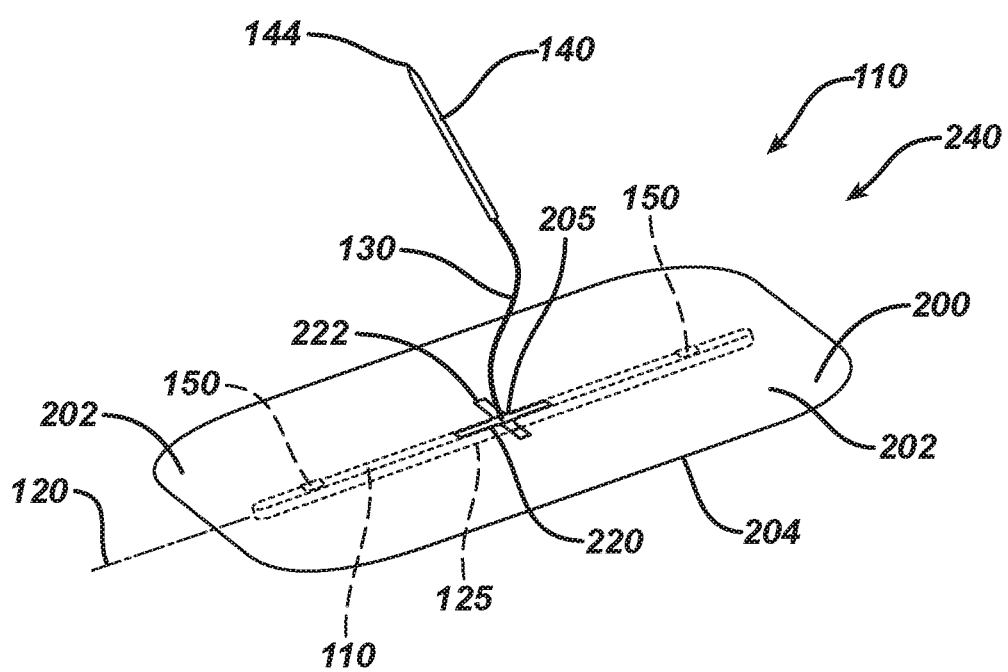
FIG. 7 shows the positioning system fully mounted to the bottom side of the mesh implant with the needle and suture completely drawn through the mesh and positioned above the top side of the mesh implant; the bar member is seen to be centrally located adjacent to the bottom side of the mesh with optional adhesive members also engaging the bottom side of the mesh.
Figure 8:
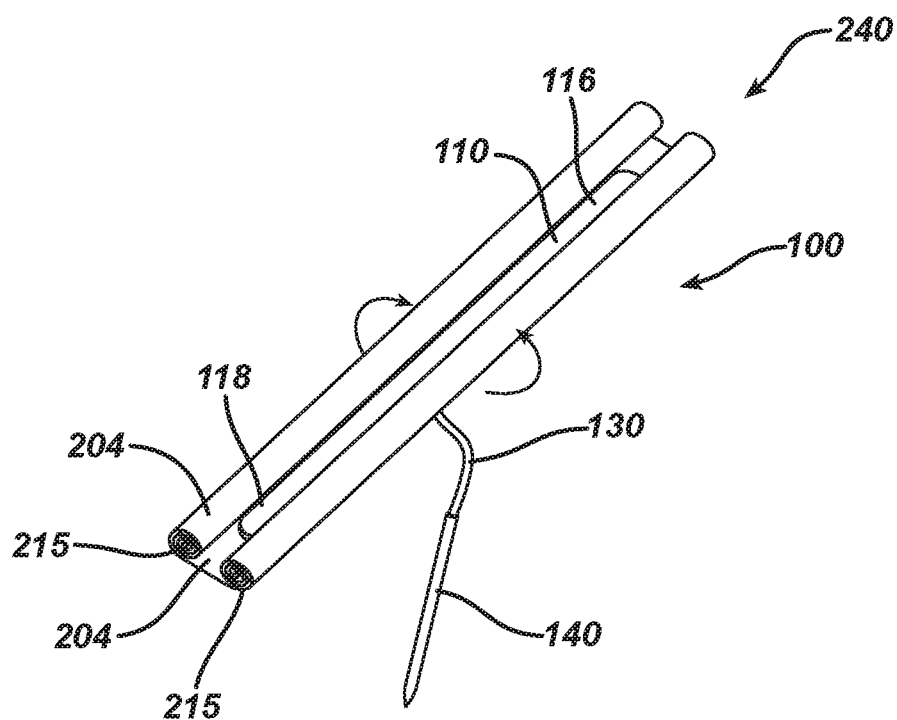
FIG. 8 is a perspective view illustrating the mesh implant and positioning system of FIG. 7, wherein the mesh implant has been rolled prior to insertion through a trocar cannula into the abdominal cavity; the attached needle and suture are seen to hang freely and the bottom of the mesh implant and the mounted bar can be seen.
Figure 9:
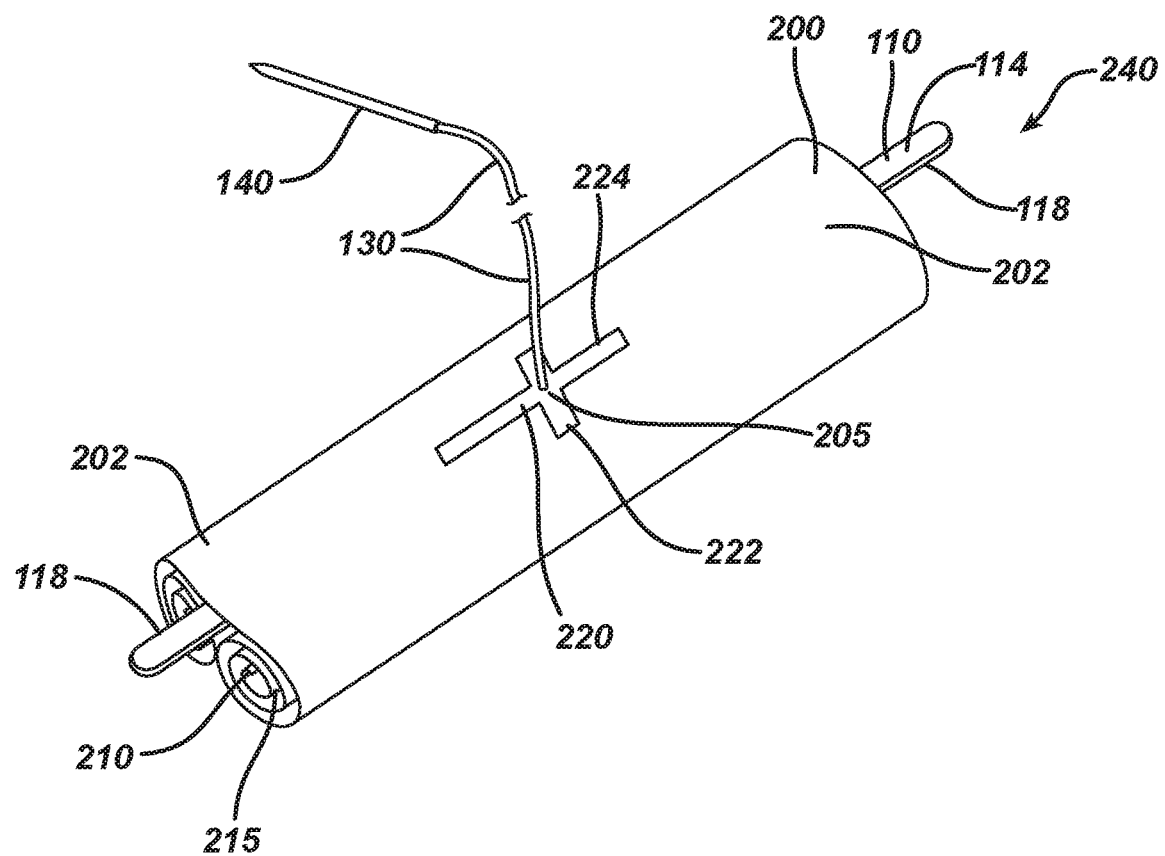
FIG. 9 is a perspective view of the mesh and positioning system assembly of FIG. 8 showing the top of the mesh and a section of suture extending outwardly from the center of the mesh.
Figure 10:
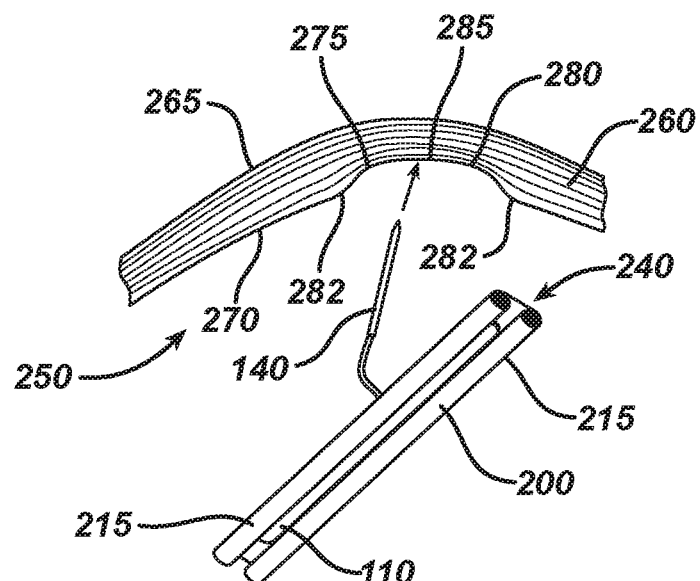
FIG. 10 shows the mesh and positioning system assembly after insertion into the abdominal cavity with the mesh in the rolled-up configuration. The assembly is positioned adjacent to the hernia defect with the needle and suture in position for the needle and suture to be passed through the hernia defect.
Figure 11:
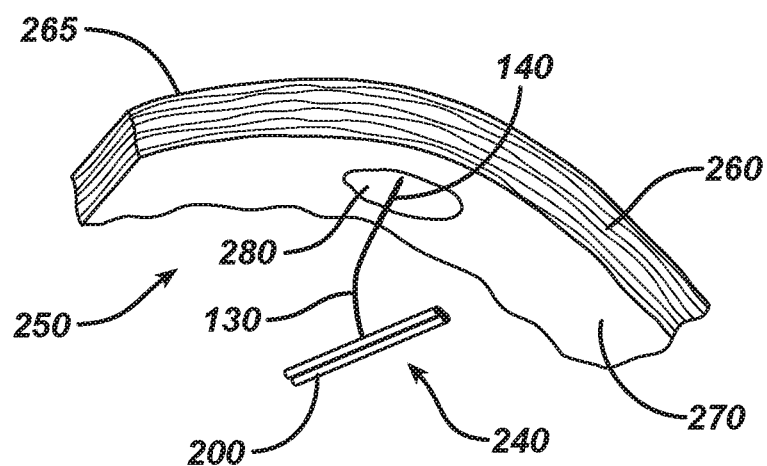
FIG. 11 shows the mesh and positioning system after the needle has been driven through the hernia defect; the mesh is still in a rolled-up configuration.
Figure 12:
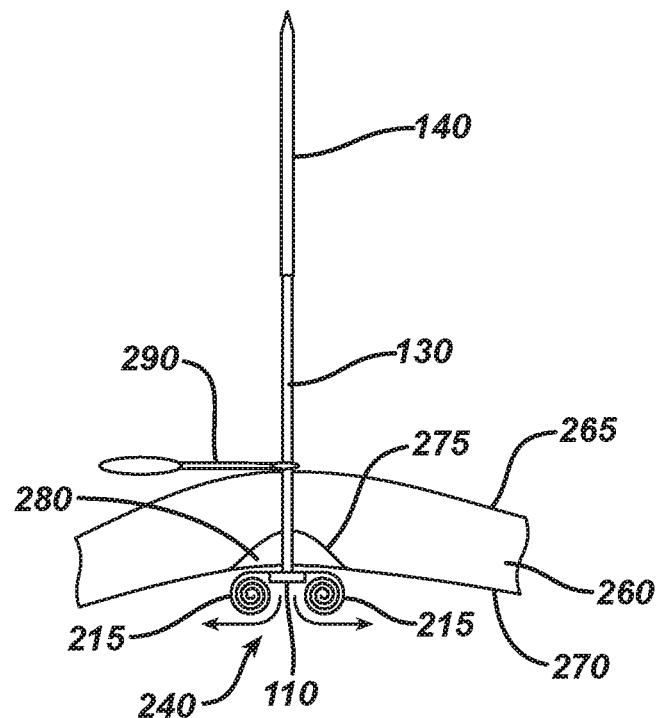
FIG. 12 is a side sectional view showing the needle and suture pulled through the defect with the suture partially exiting the defect such that the assembly is in a position over the defect adjacent to the peritoneum.

A method of affixing a mesh tissue repair implant over a defect in a body wall using the novel mesh positioning system 100 of the present invention is illustrated in FIGS. 6-14. Referring first to FIG. 6, a mesh positioning system 100 of the present invention is seen adjacent to a surgical mesh implant 200. Surgical mesh implant 200 is seen to have bottom side 204, top side 202, and center 205. The implant 200 has opposed lateral sides 210 connected by opposed end sides 212. The mesh implant 200 will typically have a flat configuration. The mesh implant 200 is seen to have location marker 220 having longitudinal marker 224 and latitudinal marker 222. The location marker 220 is centered on the mesh implant 200 such that longitudinal marker 224 and latitudinal marker 222 intersect at mesh implant center 205. The bar member 110 is mounted to the bottom 204 of mesh implant 200 by aligning the longitudinal axis 120 of bar member 110 with the longitudinal marker 224, and by aligning the center 125 of longitudinal member 110 with the center 205 of mesh implant 200. The distal end 144 of surgical needle 140 is moved or pushed through the center 125 of mesh implant 200 also moving the suture 130 through the mesh implant 200 and causing the bar member 110 to be moved proximate the bottom side 204 of mesh implant 200. Then, the top side 114 of bar member 110 is pushed against the bottom side 204 of mesh member 200 such that adhesive sections 150 releasably engage sections of bottom side 204 to form the assembly 240. The resulting assembly 240 is now ready for use in a laparoscopic body wall defect surgical procedure, such as a hernia repair procedure. In order to insert the assembly through a conventional trocar cannula, it is necessary for the assembly 240 to be rolled up. A preferred way to roll the assembly 240 is seen in FIGS. 8 and 9. The assembly 240 is placed by the surgeon on a flat surface such that the top surface 202 of mesh 200 is adjacent to the flat surface. Then, the mesh 200 is rolled about bar member 110 by grasping both lateral sides 210 and rolling the sides inwardly to form rolls or rolled sections 215 adjacent to lateral sides 118 of bar member 110.

Figure 13:
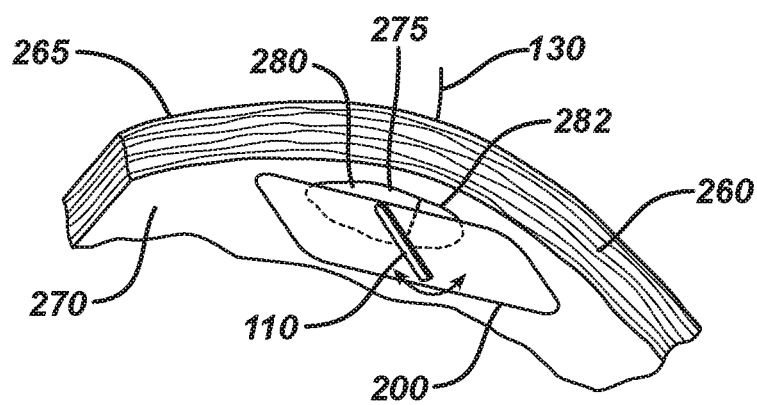
FIG. 13 is an interior perspective view showing clocking of the bar member to orient the mesh implant to an appropriate position over the body wall defect; the mesh is unrolled and has been placed back into a substantially flat configuration.
Figure 14:
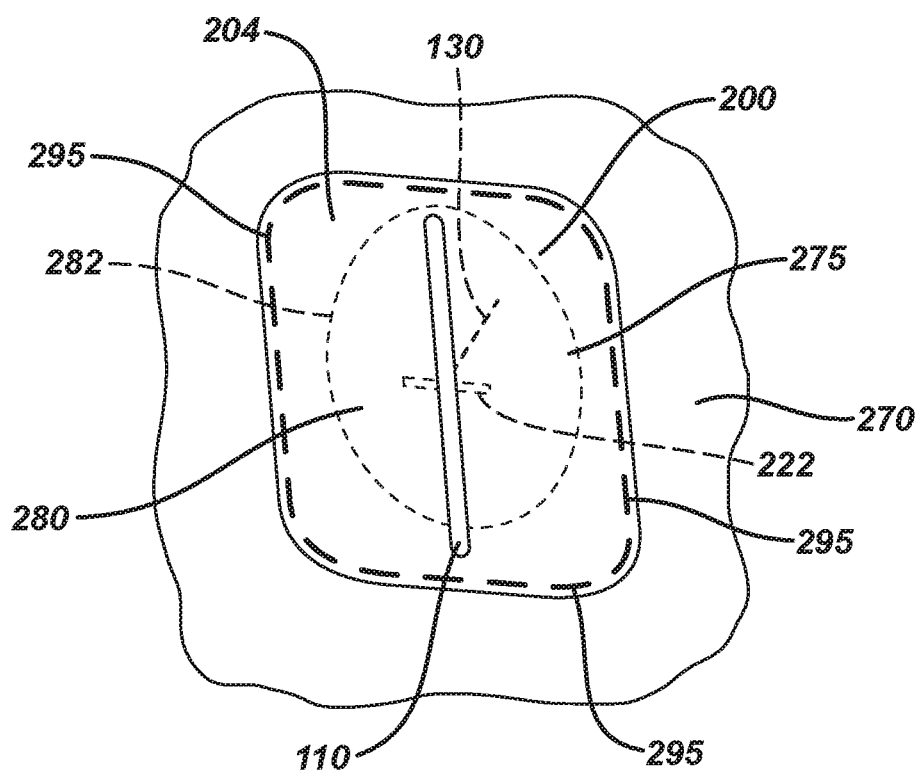
FIG. 14 is a view from the interior of the patient's abdominal cavity that shows the assembly in position over the body wall defect after the periphery of the mesh implant has been secured with surgical tacks and prior to removal of the positioning apparatus.

As seen in FIGS. 10-14, the surgeon inserts the rolled assembly 240 into a patient's abdominal cavity 250. Abdominal cavity 250 is seen to be surrounded by abdominal wall 260 having inner peritoneal layer 270 and outer epidermal layer 265. A body wall defect 280 is seen to protrude into body wall 260 along with a section of peritoneum 270 creating hernia sack 275. The body wall defect 280 has outer periphery 282. The surgeon then locates the center 285 of the defect 280 and pushes the needle 140 and suture 130 through the defect 280, through the hernia sack 275, and though body wall 260 such that the needle 140 exits the epidermal layer 265 of the body wall 260 along with a section of suture 130 and the top side 202 of the mesh 200 is positioned next to the peritoneum 270. The surgeon positions assembly 240 such that the mesh 200 is properly aligned with the defect 280 about the defect center 285. The surgeon then pulls on the needle 140 and attached suture 130 to assure that the top side 202 of mesh implant 200 is in apposition to the body wall 260 and peritoneal layer 270. The suture 130 is then clamped adjacent to epidermal layer 265 using a surgical device such as a conventional hemostat 290 or other appropriate surgical instrument or device. The rolled mesh 200 and attached bar member 110 are clocked or rotated into the appropriate orientation to cover the hernia defect 280. The surgeon then unrolls the rolled sections 215 such that the top surface 202 of the mesh 200 is in contact with peritoneum 270 and the mesh implant 200 extends sufficiently beyond the periphery 282 of hernia defect 280 to provide a margin for affixation, preferably with surgical tacks. Next, as seen in FIG. 13 the unrolled mesh 200 is affixed about its periphery with conventional surgical tacks 295. After successful placement and fixation of the mesh 200 the bar member 110 and the remaining segment of suture 130 are pulled backward away from the body wall 260 and removed from the abdominal cavity 250.

Figure 15:
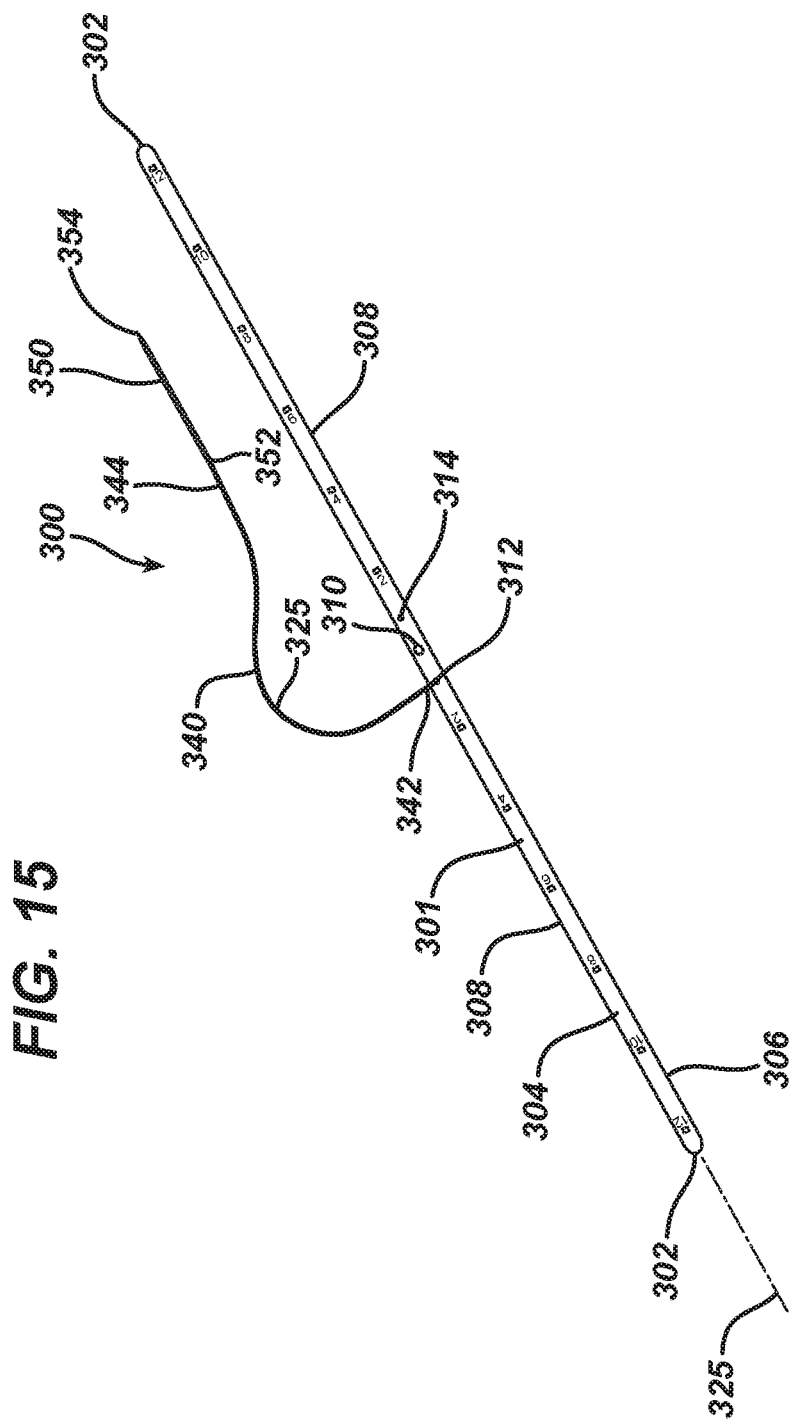
FIG. 15 is a perspective view of an alternate embodiment of a positioning system having a single bar.
Figure 16:
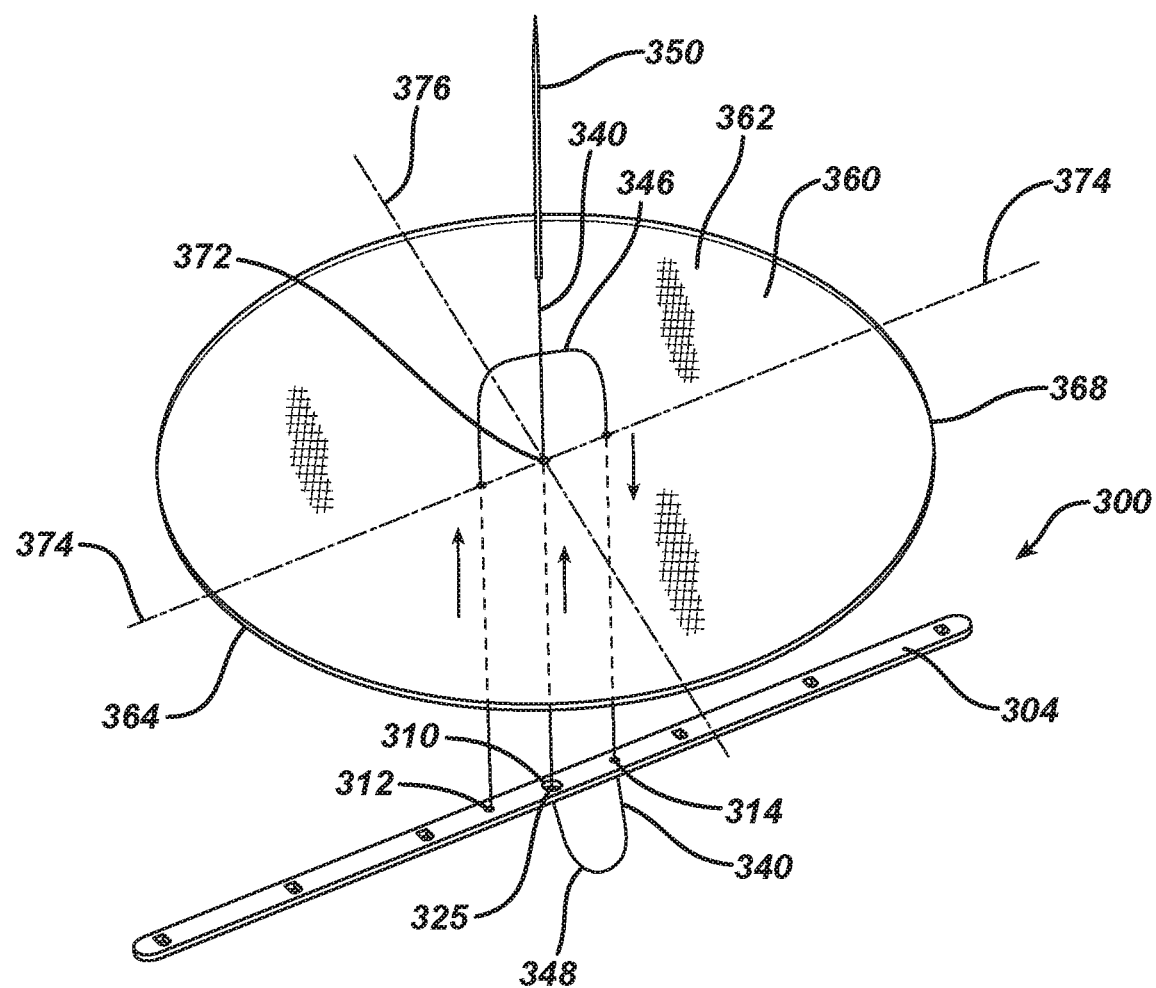
FIG. 16 illustrates the positioning system of FIG. 15 being mounted to a single layer hernia mesh implant.
Figure 17:
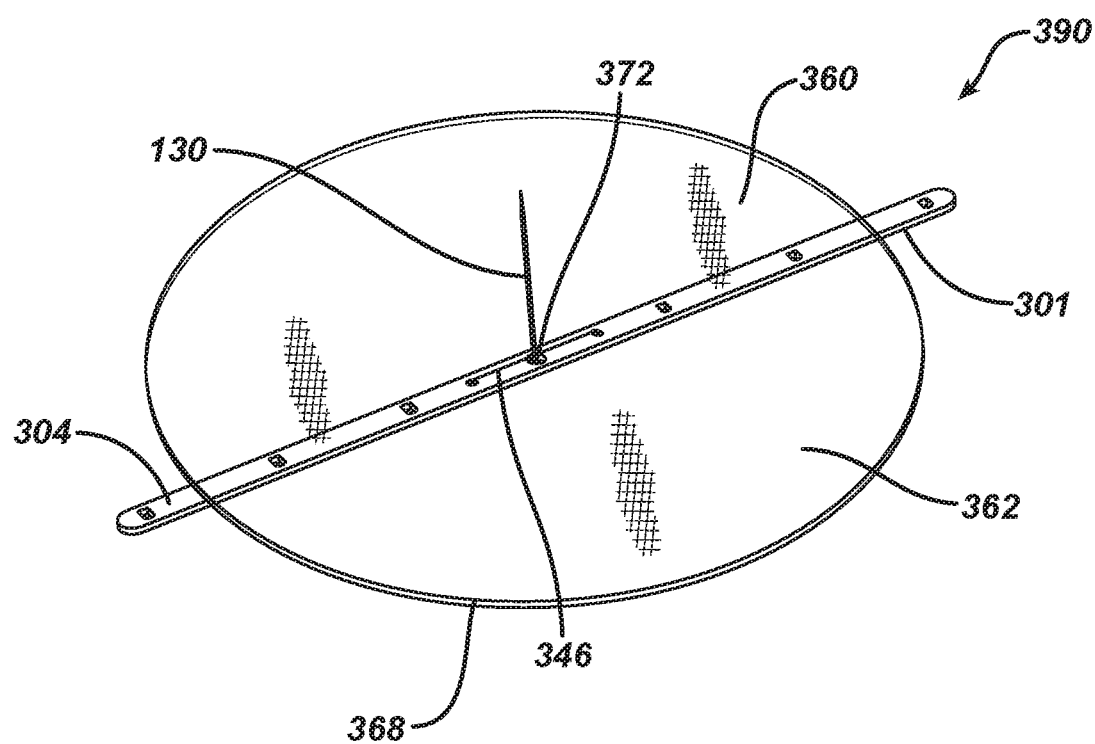
FIG. 17 illustrates the positioning system and mesh of FIG. 16 after the assembly has been completed. The mesh implant is drawn substantially transparent to illustrate the underlying positioning system.
Figure 18:
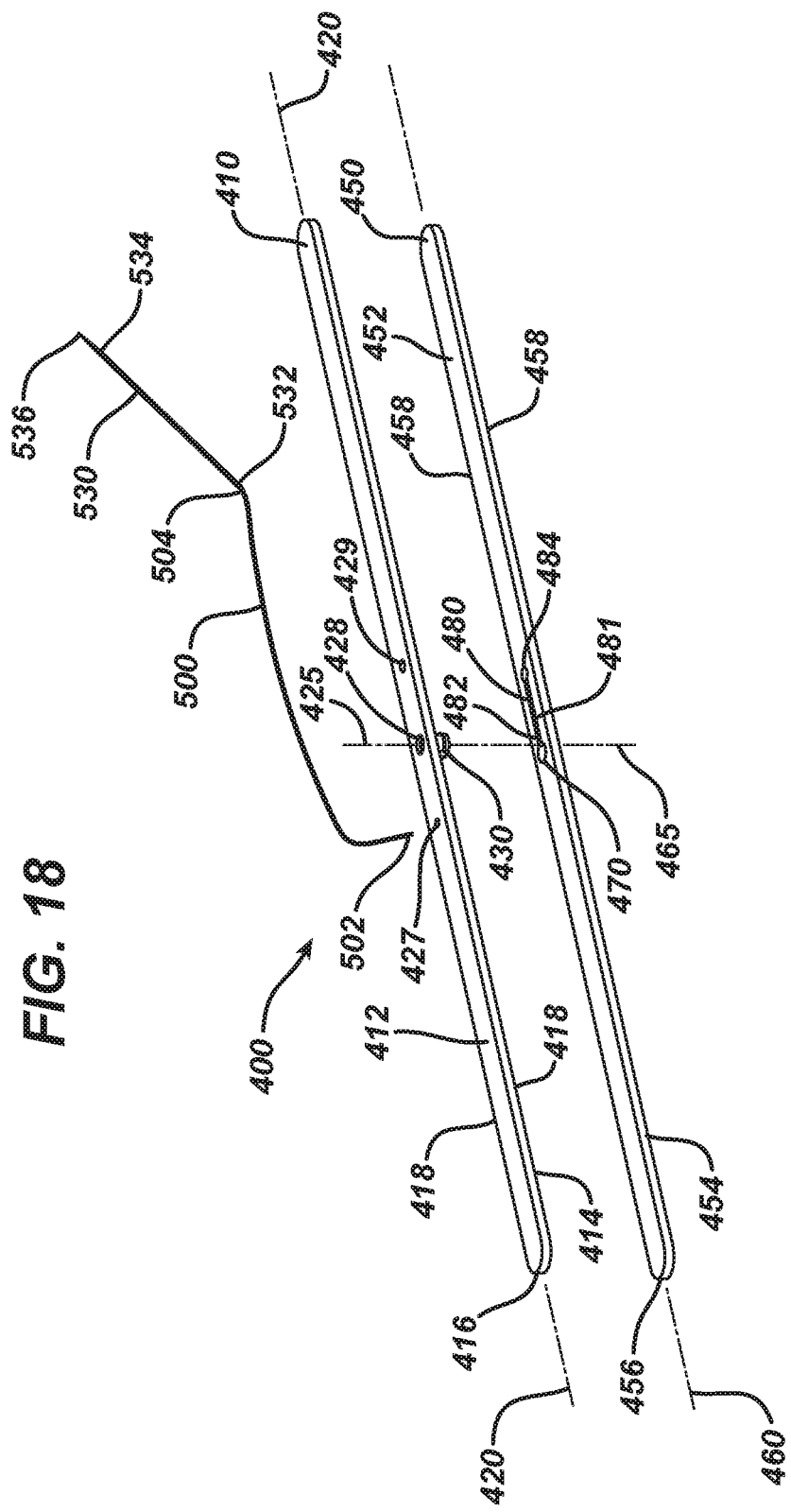
FIG. 18 is an exploded perspective view of an alternate embodiment of a double bar positioning system of the present invention.
Figure 18A:
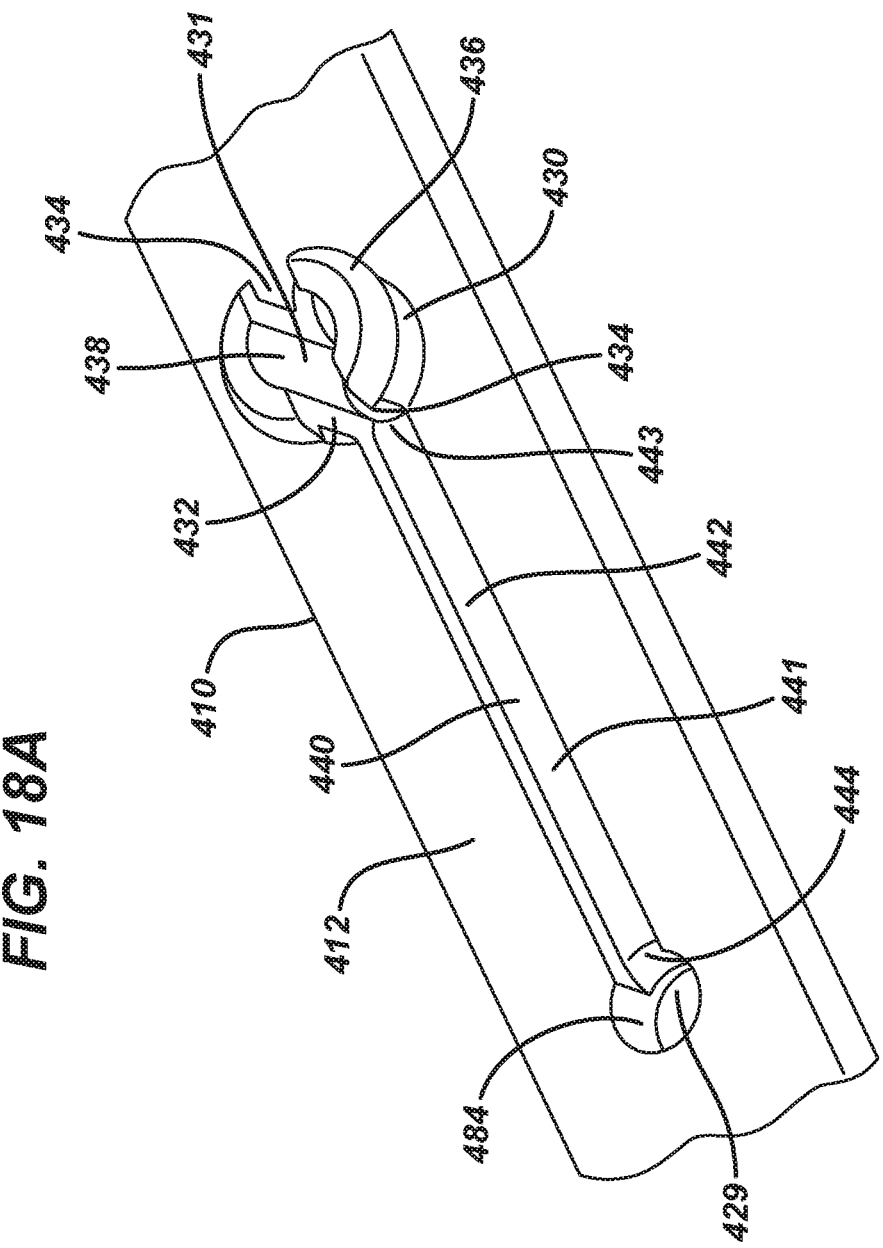
FIGS. 18A and 18B are partial perspective views of the bottom of the top bar of the positioning system of FIG. 18 showing the pivot hub and suture passing holes and a slot for receiving a suture segment.
Figure 18B:
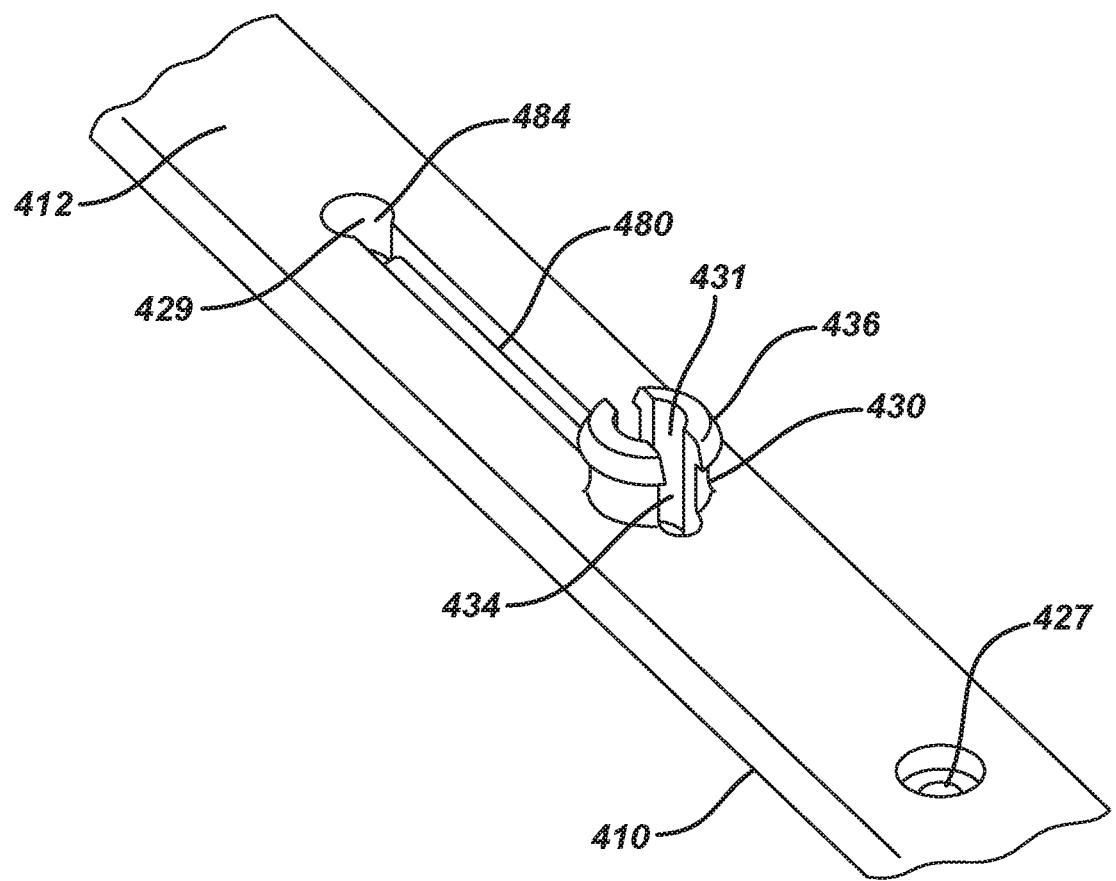
Figure 20:
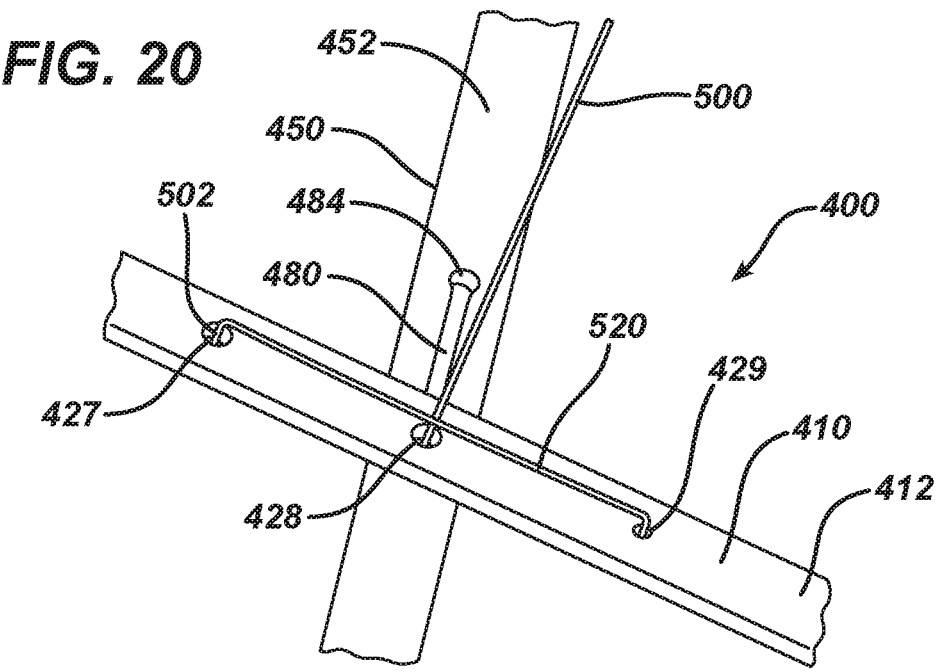
FIG. 20 is a magnified partial top view of the center section of the assembly of FIG. 19 showing a surgical suture mounted to the assembly.
Figure 21:
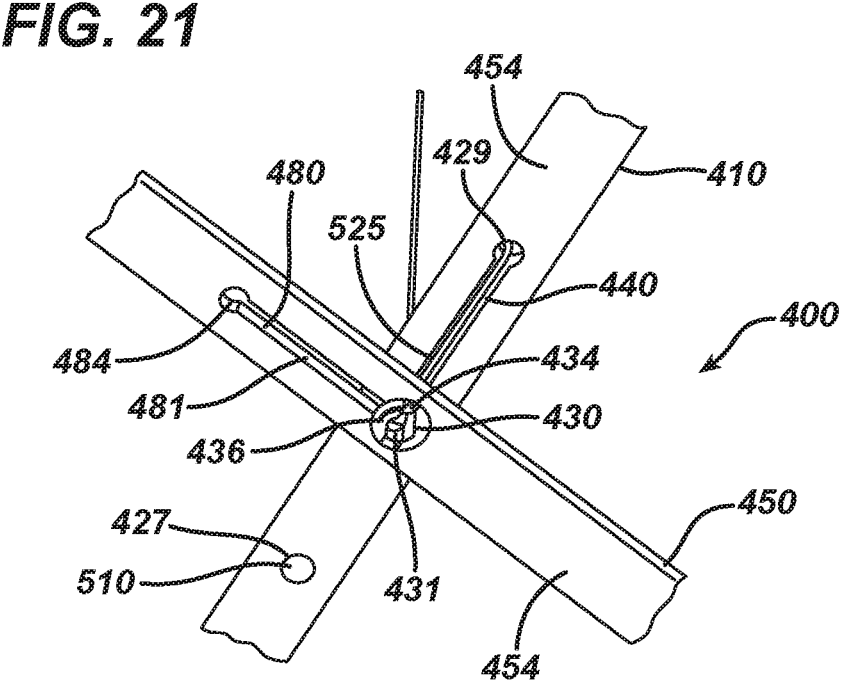
FIG. 21 is a magnified partial bottom view of the center section of the assembly of FIG. 19 showing a surgical suture mounted to the assembly.
Figure 22:
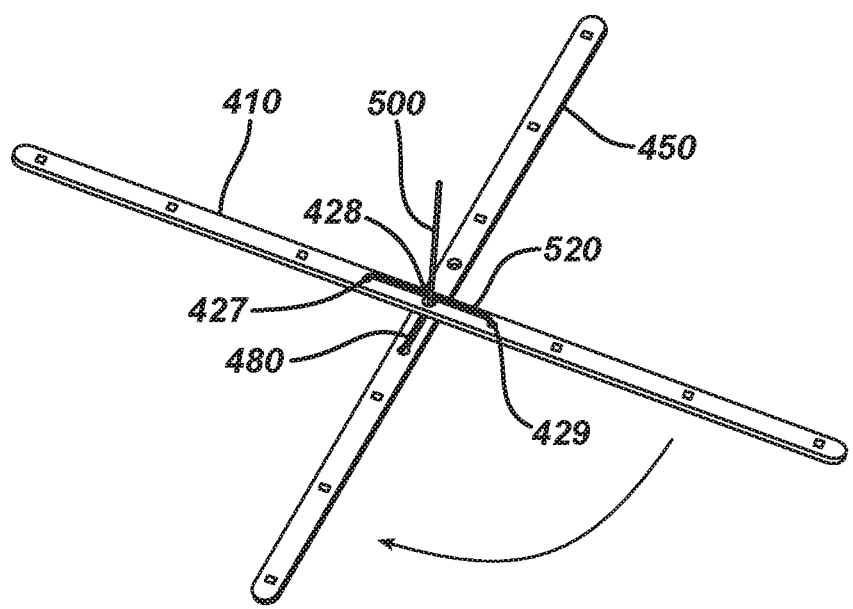
FIG. 22 is a perspective view of the positioning system of FIG. 19 showing the rotational capacity of the bottom bar.
Figure 23:
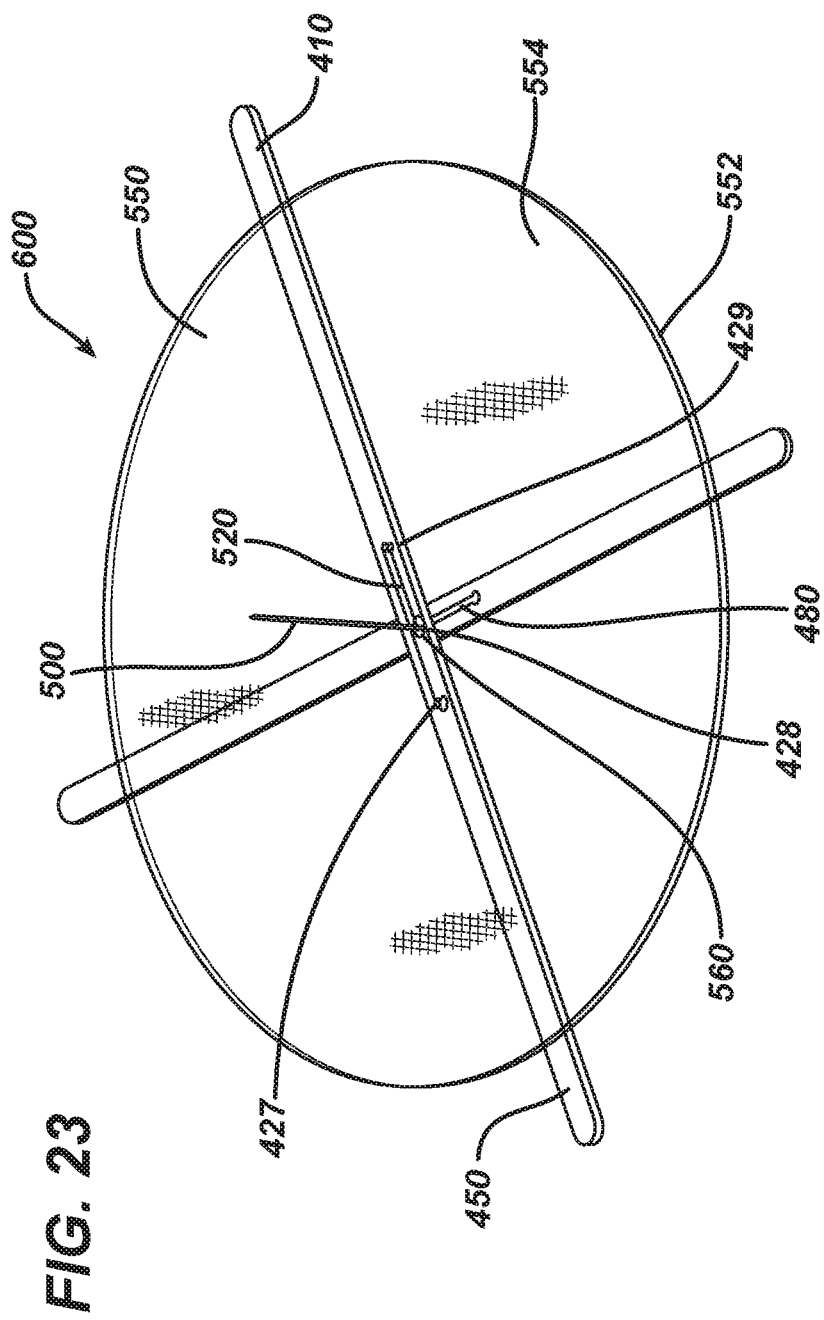
FIG. 23 is a perspective view showing the positioning system of FIG. 19 mounted to a flat, single layer mesh implant. The mesh implant is drawn substantially transparent to illustrate the underlying positioning system.
Figure 24:
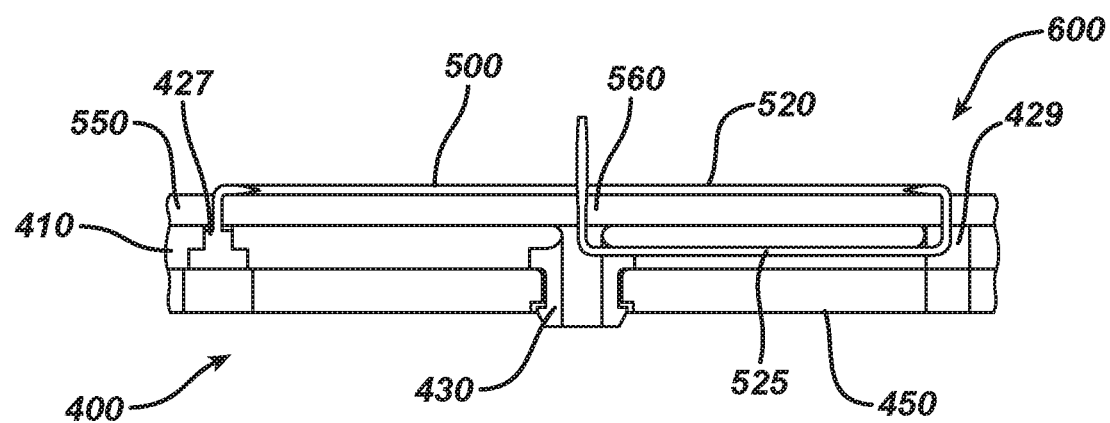
FIG. 24 is a side partial cross-sectional view of the central section of the assembly of FIG. 19 with both bars in longitudinal alignment.
Figure 25:
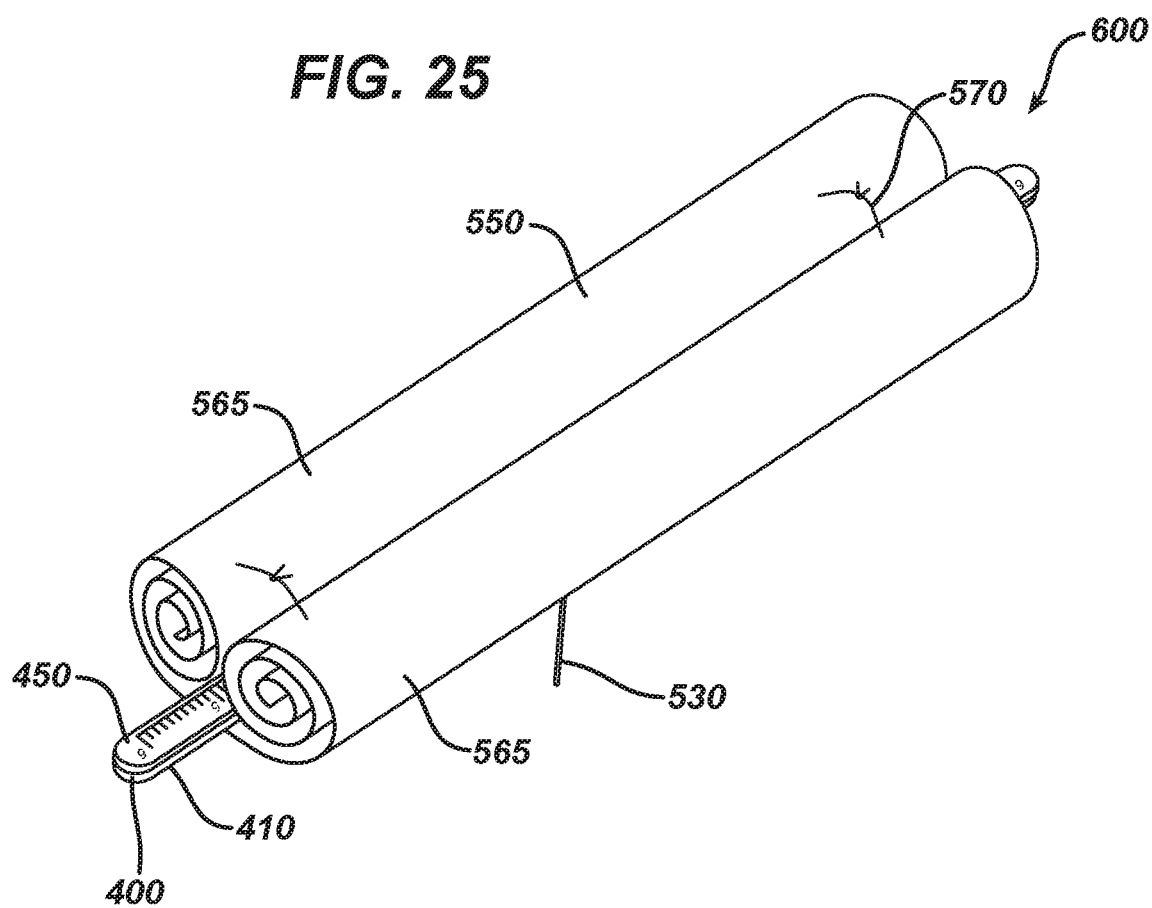
FIG. 25 is a perspective view of the assembly of FIG. 23 rolled in preparation for insertion through a trocar cannula.

An alternative embodiment of a mesh positioning system 300 having a bar member 301, surgical suture 340, and surgical needle 350 useful in the practice of the present invention is illustrated in FIGS. 15-17. The bar member 301 is seen to have opposed rounded ends 302. Bar member 301 has top side 304 and bottom side 306, and opposed lateral sides 308. The bar member 301 has longitudinal axis 320 and center 325. The center hole 310 extends through bar member 301 at center 325. Suture attachment hole 312 and suture passing hole 314 are located adjacent to and on either side of center hole 310; holes 312 and 314 pass through bar member 301. The proximal end 342 of surgical suture 340 is attached to bar member 301 in suture attachment hole 312 and is seen to extend from suture attachment hole 312 from top side 304 of bar member 301. The distal end 344 of suture 340 is mounted to the proximal end 352 of straight surgical needle 350 having distal piercing point 354. The positioning system 300 is mounted to surgical repair mesh 360 to form assembly 390. The mesh 360 is seen to have top side 362 and bottom side 364. The mesh 360 has center 372, major axis 374 and minor axis 376. Mesh 360 has outer periphery 368. In order to mount positioning system 300 to mesh 360 to form assembly 390, the longitudinal axis 325 of bar member 301 is aligned with major axis 374 of mesh 360. The top side 304 of bar member 301 is placed adjacent to bottom side 364 of mesh 360 such that the centers 325 and 372 are in substantial alignment. Next, the piercing point 354 of needle 350 is pushed through mesh 360 from the bottom side 364 at a location adjacent to center 372, and the suture 340 is pulled through. The needle 350 is then passed down from top side 362 through mesh 360 and through opening 314 in bar member 301 forming top suture segment 346. The needle 350 is then passed from the bottom side 306 of bar member 301 through center opening 310 and through mesh 360 along with the remaining suture 340. Suture segment 348 is formed on bottom side 306. This completes the assembly of the assembly 390. The assembly 390 is used in a manner similar to assembly 240 as described above.

An alternative embodiment of a double bar mesh positioning system 400 of the present invention is seen in FIGS. 18-25. The positioning system 400 is seen to have top bar member 410 and bottom bar member 450. Top bar member 410 is seen to have top side 412, bottom side 414, and opposed ends 416 connecting opposed lateral sides 418. The bar member 410 has longitudinal axis 420 and center 425. Suture passing holes 427 and 429 extend through bar member 410. Extending downwardly from the bottom side 414 of bar member 410 and coextensive with center 425 is the pivot hub member 430. Hub member 430 is seen to have a generally cylindrical configuration with lateral side slots 434 in communication with central passage 431. Flange member 436 is seen to extend about the bottom end 432 of hub member 430. Passage 438 is seen to extend up through bar member 410 and to be in communication with central suture passing hole 428. Contained in the bottom 414 of bar member 410 is the suture receiving slot 440. Slot 440 has bottom 441, channel 442, first end 443 in communication with lateral slot 434 of hub member 430 and second end 444 in communication with suture passing hole 429. Bottom bar member 450 is seen to have top side 452, bottom side 454, and opposed ends 456 connecting opposed lateral sides 458. The bar member 450 has longitudinal axis 460 and center 465. Pivot hub receiving hole 470 is seen to extend through bar member 450 and is located at the center 465. The bar member 450 is also seen to have suture passage slot 480 extending through bar member 450. The slot 480 has channel 481, first end 482 in communication with pivot hub receiving hole 470 and second rounded end 484 in communication with suture opening 429. The bar members 410 and 450 are pivotally mounted to each other by forcing the end of hub member 460 into hub receiving hole 470 such that the flange member 436 is engaged on or below the bottom side 454 of bar member 450. A surgical suture 500 having a proximal end 502 and a distal end 504 is mounted to opening 427 such that the suture extends from opening 427 above top side 412 of bar member 440. This may be accomplished by mounting a plug like member 510 to proximal end 502 or by knotting the end 502. The proximal suture end 502 can also be glued or cemented into opening 427. The distal end 504 of suture 500 is mounted to the proximal end 532 of surgical needle 530 having distal end 534 and distal piercing distal tip 536.

The system 400 is mounted to a surgical repair mesh 550 to form a repair assembly 600 in the following manner. The bar members 410 and 450 are manipulated such that the longitudinal axes 420 and 460 are in alignment. Next the center 425 of bar member 410 is aligned with the center 560 of mesh 550. The surgical needle 530 attached to suture 500 is then pushed through mesh 550 from bottom side 552 through top side 554. The needle 530 is then pushed through the top side 554 of mesh 550 through underlying suture passing hole 429 and through opening 484 in bar members 410 and 450, respectively, and a length of free suture 500 is also moved through forming top suture segment 520. Next the needle 530 is moved through pivot hole 470 and out through central passage 431 and central suture passing hole 428. As the suture 500 is withdrawn, a section of the suture 500 will pass through slot 434 and channel 481 in slot 480, and as the suture 500 is further withdrawn and tightened suture segment 525 will move into channel 442 of slot 440. The top side 414 of bar member 410 will now be engaged with the bottom side 552 of mesh 550. The mesh may be rolled about the positioning system 400 to form rolls 565 to facilitated passage through a cannula into the abdominal cavity. If desired, the rolls 565 may be optionally secured with sutures 570, which are then removed prior to unrolling the mesh 550 after movement through a cannula. The repair assembly 600 is used in a manner similar to that described above for assembly 400, except that the bars 410 and 450 may be pivoted or rotated, sometimes described as "clocked", with respect to each other to further support the mesh 550 and aid in placement over to the body wall defect next to the peritoneum. Optionally, as partially shown in FIG. 25, the bar members may be provided with measurement scale markings to indicate the lengths of the bars and the lengths of the attached meshes. Alternate conventional ways of pivotally mounting the bar members 410 and 450 together may be utilized including bolts, axles, pins, rivets, etc.

Although it is preferred that the surgical sutures useful with the positioning systems and repair assemblies of the present invention have surgical needles mounted to an end, it will be appreciated that surgical sutures may be utilized without mounted surgical needles. In such a configuration, the suture would be passed through tissue and/or the implant using conventional surgical instruments such as conventional suture passing instruments. Also, if desired although not preferred, multiple sutures may be used with the positioning systems of the present invention.

The following example is illustrative of the principles and practice of the present invention, although not limited thereto.

Example 1

A patient presenting with a ventral hernia is prepared for a laparoscopic surgical hernia repair procedure in a conventional manner. After conventional preparation and administration of conventional anesthesia, the surgeon insufflates the patient's abdominal cavity using a conventional Veress needle attached to a medical grade carbon dioxide gas source. After insufflation, the surgeon inserts several trocar cannulas through the abdominal wall using conventional trocars. The trocar cannulas provide access to the abdominal cavity and access to the surgical site. A conventional laparoscope is inserted into one of the cannulas and connected to a camera to provide the surgeon with remote visualization. The surgeon views the hernia defect in the patient's abdominal wall and measures the defect with a surgical ruler. The surgeon then selects an appropriately sized surgical hernia defect repair mesh implant. The surgeon is provided with a mesh positioning system of the present invention having a single bar member. After determining the center of the mesh implant, the surgeon pushes the surgical needle and suture of the positioning system through the bottom side of the mesh implant at the center and pulls the needle and suture until the top surface of the bar member is next to and in contact with the bottom side of the mesh implant. The surgeon then aligns the bar member with the longitudinal axis of the mesh implant and applies force to the top side of the mesh over the optional adhesive sections on the top side of the bar member to secure the mesh to the positioning system. The surgeon then rolls the sides of the mesh about the centrally located bar member in order to move the positioning system and mesh assembly through a conventional trocar cannula into the patient's abdominal cavity. The mesh of the assembly is unrolled using conventional laparoscopic grasping tools. The assembly is then moved toward the defect and the mesh is placed in apposition to the peritoneum adjacent to the hernia defect. The surgeon then grasps the surgical needle with a laparoscopic needle grasper instrument and pushes the needle and a section of the suture through the hernia defect and the hernia sack and body wall tissue layers over the defect. The needle is then grasped exterior to the body wall and tensioned such that the top side of the mesh is moved against the interior of the abdominal wall (i.e., the peritoneum) and the edges of the defect are overlapped by the mesh in the surrounding peritoneum. The tensioned suture is maintained in position by applying a surgical hemostat to the protruding suture, and the needle is cut away from the suture. The surgeon then views the position of the mesh implant over the body wall tissue defect and makes positional changes as required. The mesh is observed to be maintained in a flat configuration against the peritoneum with substantially no wrinkles. The surgeon then inserts the distal end of a conventional surgical tacking instrument into the patient's abdominal cavity and proceeds to tack the mesh implant about its entire periphery with a continuous line of spaced apart tacks. The surgeon then removes the mesh positioning system from the bottom of the mesh implant by disengaging the hemostat from the exterior section of suture and pulling the bar member away from the implant thereby pulling the remaining suture segment back into the abdominal cavity. The positioning system is then removed through a cannula. Then, the instruments, cannulas and Veress needle are removed from the patient. The trocar incisions for the cannulas are then taped with conventional surgical tape and the repair procedure is complete. Alternatively, if there is no surgical needle attached to the suture of the positioning system, a conventional suture passer can be used by the surgeon to pull the suture through the abdominal wall and position the mesh on the interior of the body wall. Prior to affixing the mesh implant to the body wall over the defect, the surgeon may decide to optionally remove all or part of the hernia sack. In addition, the surgeon may decide to suture the tissue surrounding the hernia defect together prior to affixing the mesh implant.

Although this invention has been shown and described with respect to detailed embodiments thereof, it will be understood by those skilled in the art that various changes in form and detail thereof may be made without departing from the spirit and scope of the claimed invention.

We claim:

1. A surgical repair assembly, comprising:
   a substantially flat surgical repair mesh having a top side adapted to be placed against an abdominal wall of a patient, a bottom side, a center, a major axis and a minor axis;
   a positioning system comprising a bar member having substantially flat top and bottom sides, a center, first and second opposite ends extending along a longitudinal axis, a suture receiving opening centrally located in the bar member, and first and second adhesive sections located on the top side of the bar member near the first and second ends thereof; and
   a surgical suture having a distal end and a proximal end, wherein the proximal end of the suture is mounted in the suture receiving opening such that the suture extends out from the top side of the bar member;
   wherein the top side of the bar member engages the bottom side of the surgical repair mesh such that the longitudinal axis of the bar member is substantially aligned with the major axis of the surgical repair mesh and the surgical suture passes through the center of the surgical repair mesh, and wherein the first and second adhesive sections of the bar member releasably engage the bottom side of the surgical repair mesh.

2. The surgical repair assembly according to claim 1, wherein the suture receiving opening of the bar member is a bore hole.

3. The surgical repair assembly according to claim 1, further comprising a surgical needle mounted to the distal end of the suture.

4. The surgical repair system according to claim 1, wherein the surgical repair mesh is rolled about the bar member.

5. The surgical repair system according to claim 1, wherein the surgical repair mesh has first and second lateral sides including first and second ends of the minor axis respectively, and wherein the first lateral side of the surgical repair mesh is rolled about a first lateral side of the bar member and the second lateral side of the surgical repair mesh is rolled about a second lateral side of the bar member.

6. A method for performing a laparoscopic body wall defect repair procedure, comprising the steps of:
   inserting the surgical repair assembly of claim 1 into a body cavity of a patient,
   positioning the assembly adjacent a body wall defect such that the top side of the surgical repair mesh is adjacent to the defect;
   driving the suture through the defect and overlying body wall such that a section of suture exits the body wall and body cavity;
   tensioning the suture such that the top side of the mesh is held in contact with the body wall surrounding the defect via the bar member; and
   securing the mesh over the defect.

7. The method according to claim 6, further comprising the step of removing the bar member and mounted surgical suture from the body cavity.

8. A method for performing a laparoscopic body wall defect repair procedure, comprising the steps of:
   inserting the surgical repair assembly of claim 1 into a body cavity of a patient,
   positioning the assembly adjacent a body wall defect such that the top side of the surgical repair mesh is adjacent to the defect;
   driving the suture through the defect and overlying body wall such that a section of suture exits the body wall and body cavity;
   tensioning the suture such that the top side of the mesh is held in contact with the body wall surrounding the defect via the bar member;
   unrolling the first and second lateral sides of the surgical repair mesh; and
   securing the mesh over the defect.

* * * * *